(12) United States Patent
Endou et al.

(10) Patent No.: US 10,317,368 B2
(45) Date of Patent: Jun. 11, 2019

(54) DEFECT INSPECTION DEVICE AND DEFECT INSPECTION METHOD

(71) Applicant: HITACHI, LTD., Chiyoda-ku, Tokyo (JP)

(72) Inventors: Hisashi Endou, Tokyo (JP); Hiroyuki Takagi, Toyohashi (JP); Taichi Goto, Toyohashi (JP); Mitsuteru Inoue, Toyohashi (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 15/528,013

(22) PCT Filed: Nov. 28, 2014

(86) PCT No.: PCT/JP2014/081653
§ 371 (c)(1),
(2) Date: May 18, 2017

(87) PCT Pub. No.: WO2016/084261
PCT Pub. Date: Jun. 2, 2016

(65) Prior Publication Data
US 2017/0328864 A1 Nov. 16, 2017

(51) Int. Cl.
*G01N 27/72* (2006.01)
*G01N 27/82* (2006.01)
(Continued)

(52) U.S. Cl.
CPC ......... *G01N 27/9046* (2013.01); *G01N 27/83* (2013.01)

(58) Field of Classification Search
CPC ........ G01N 27/72; G01N 27/82; G01N 27/90; G01N 21/00; G01N 21/88; G01N 21/95; G01J 4/00
See application file for complete search history.

(56) References Cited

U.S. PATENT DOCUMENTS 5,235,400 A * 8/1993 Terasawa et al. ...... G01N 21/00
356/237
5,822,063 A 10/1998 Suzuki et al.
(Continued)

FOREIGN PATENT DOCUMENTS

JP 7-287059 A 10/1995
JP 9-280953 A 10/1997
(Continued)

OTHER PUBLICATIONS

English Translation of International Preliminary Report on Patentability from International Patent Application No. PCT/JP2014/081653, dated Jun. 8, 2017.
(Continued)

*Primary Examiner* — Neel D Shah
(74) *Attorney, Agent, or Firm* — Miles & Stockbridge P.C.

(57) ABSTRACT

A defect inspection device configured to measure a surface shape of an inspection target using light applied to the inspection target via a spatial light phase modulator based on an interference state of reflected light from the inspection target obtained via the spatial light phase modulator, to measure magnetic field distribution of a surface of the inspection target magnetized by an excitation device for magnetizing the inspection target using light applied to the inspection target via the spatial light phase modulator based on an interference state of reflected light from the inspection target obtained via the spatial light phase modulator, and to separate data of a magnetic field specific portion which exists on the surface of the inspection target from magnetic field distribution data which is a measurement result of magnetic field distribution of the inspection target based on surface shape data which is a measurement result of the surface shape of the inspection target, to suppress deterioration of measurement accuracy of magnetic field distribu-
(Continued)

tion generated by the surface shape of the inspection target and to improve defect detection accuracy.

7 Claims, 9 Drawing Sheets

(51) Int. Cl.
  *G01N 27/90* (2006.01)
  *G01N 27/83* (2006.01)

(56) References Cited

U.S. PATENT DOCUMENTS

| | | | |
|---|---|---|---|
| 2011/0001962 A1* | 1/2011 | Sasazawa | G01N 21/95692 356/237.2 |
| 2011/0310387 A1 | 12/2011 | An et al. | |
| 2012/0274937 A1* | 11/2012 | Hays | G01S 17/58 356/337 |
| 2014/0176698 A1 | 6/2014 | Banerjee et al. | |
| 2014/0225606 A1 | 8/2014 | Endo et al. | |
| 2015/0285744 A1* | 10/2015 | Ogawa | G02B 27/283 348/126 |

FOREIGN PATENT DOCUMENTS

| | | |
|---|---|---|
| JP | 2005-315590 A | 11/2005 |
| JP | 2010-537355 A | 12/2010 |
| JP | 2014-155318 A | 8/2014 |

OTHER PUBLICATIONS

Extended European Search Report dated May 2, 2018 for corresponding European Patent Application No. 14906922.1.

* cited by examiner

[Fig. 1]
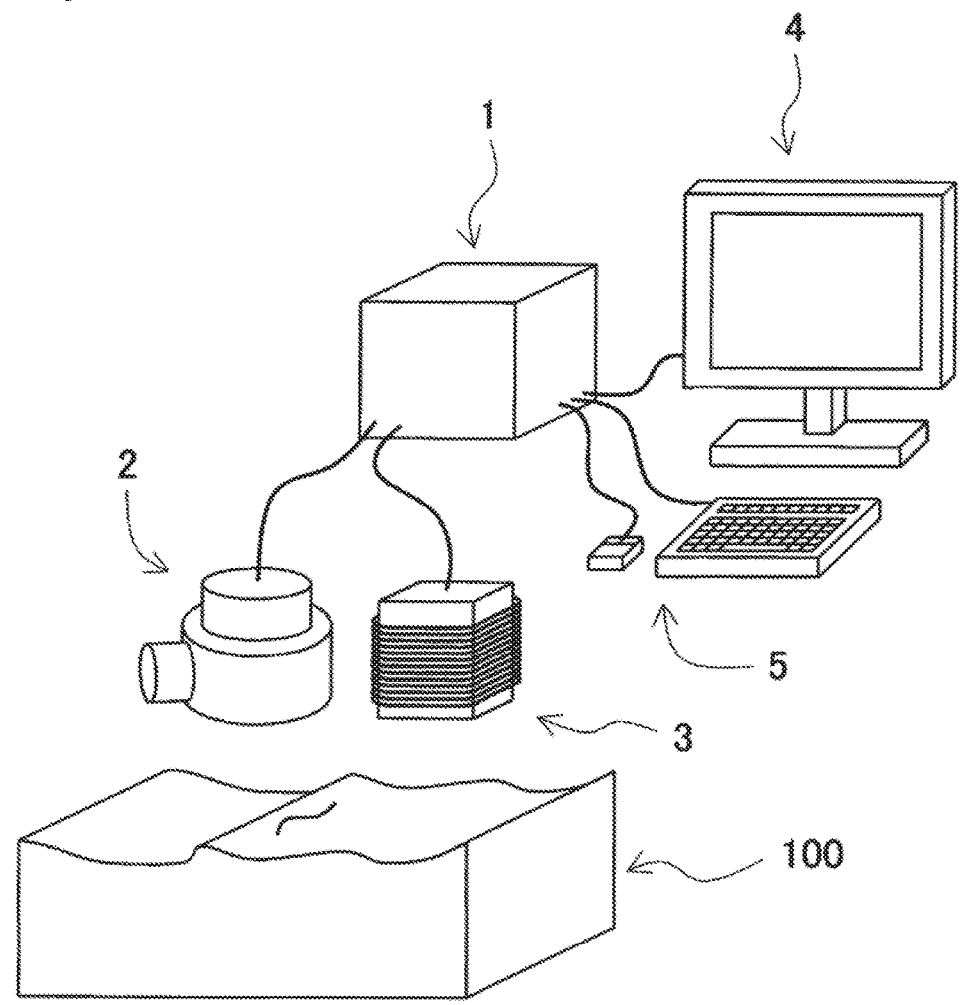

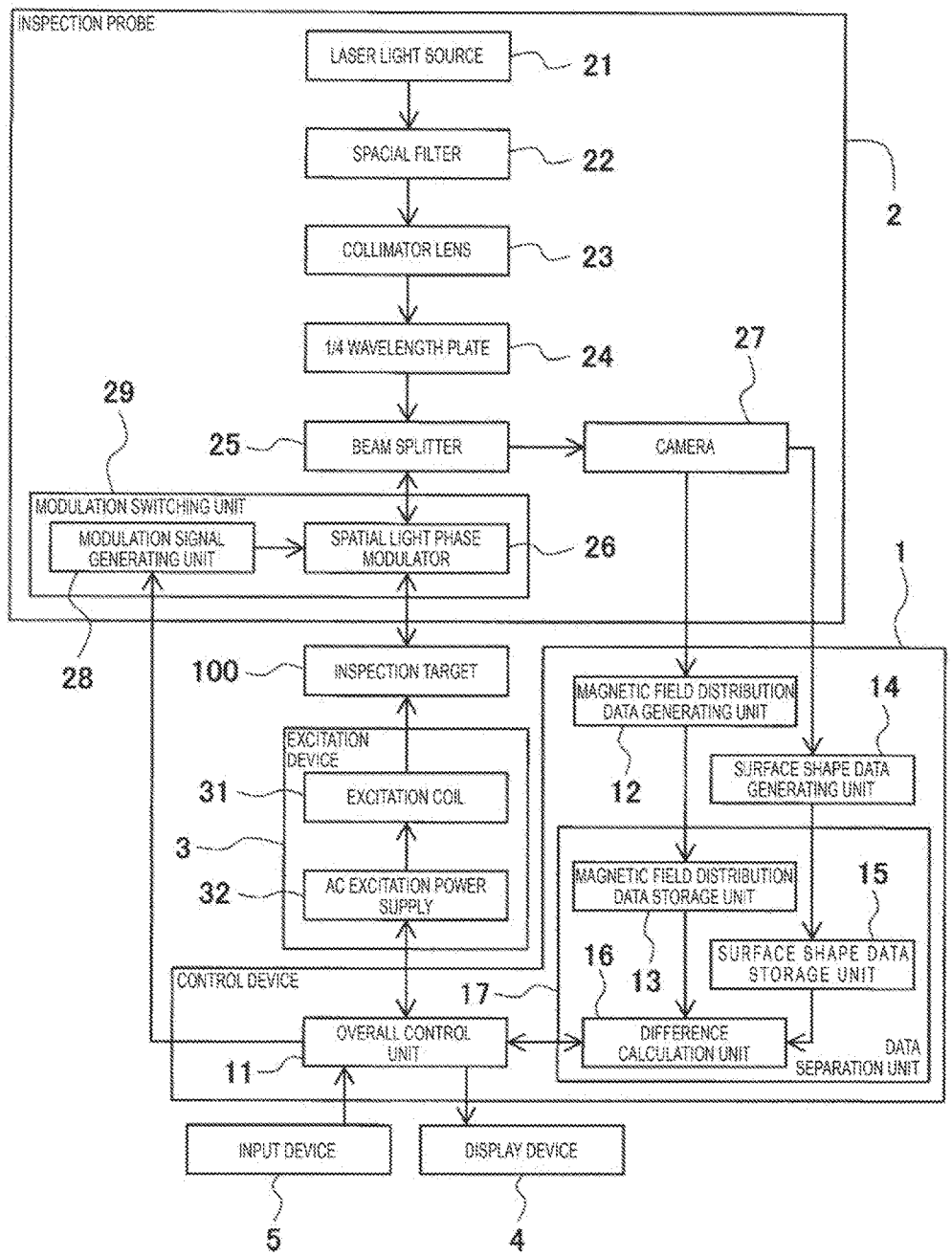
[Fig. 2]

[Fig. 3]
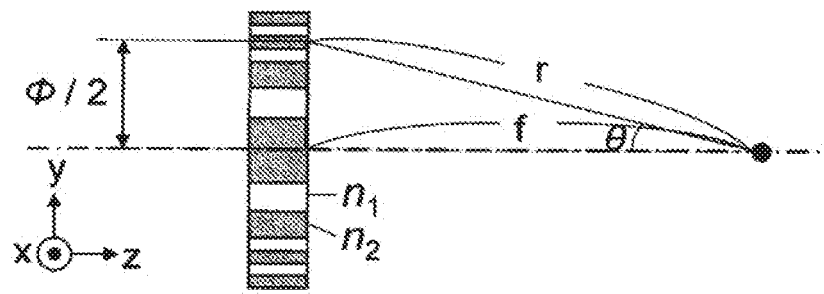
[Fig. 4]
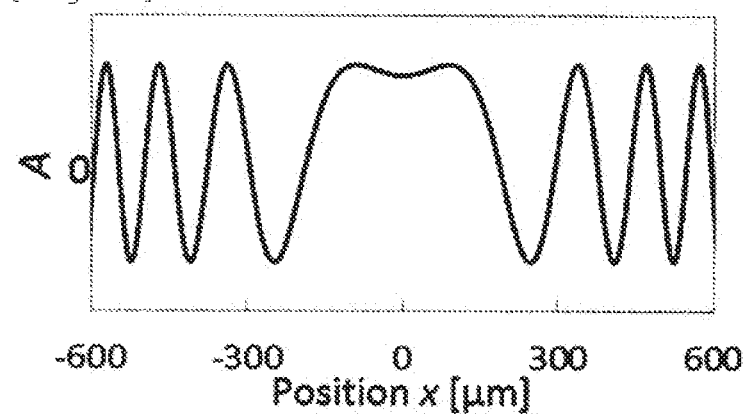
[Fig. 5]
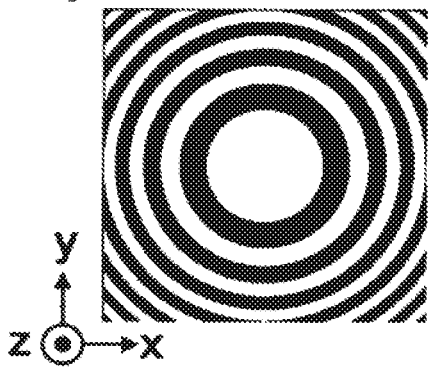

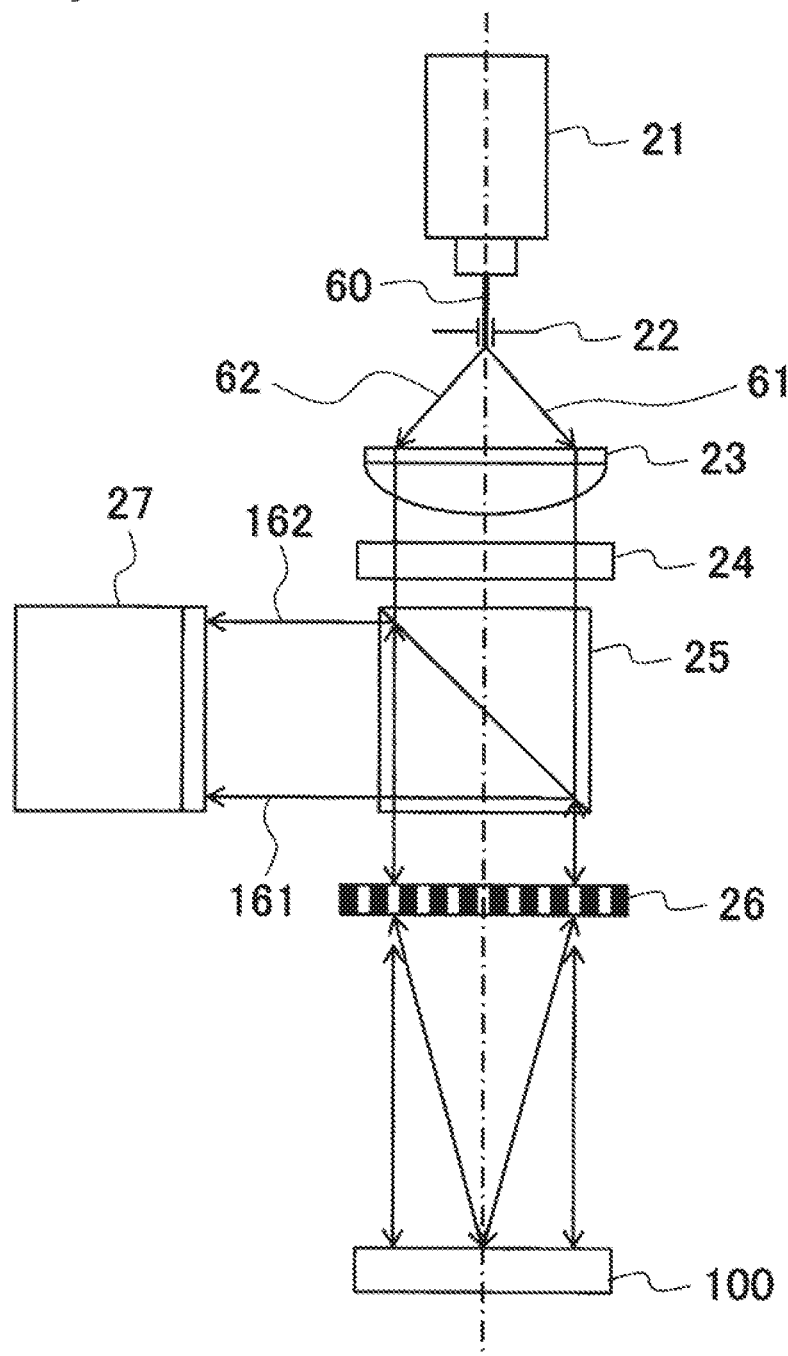
[Fig. 6]

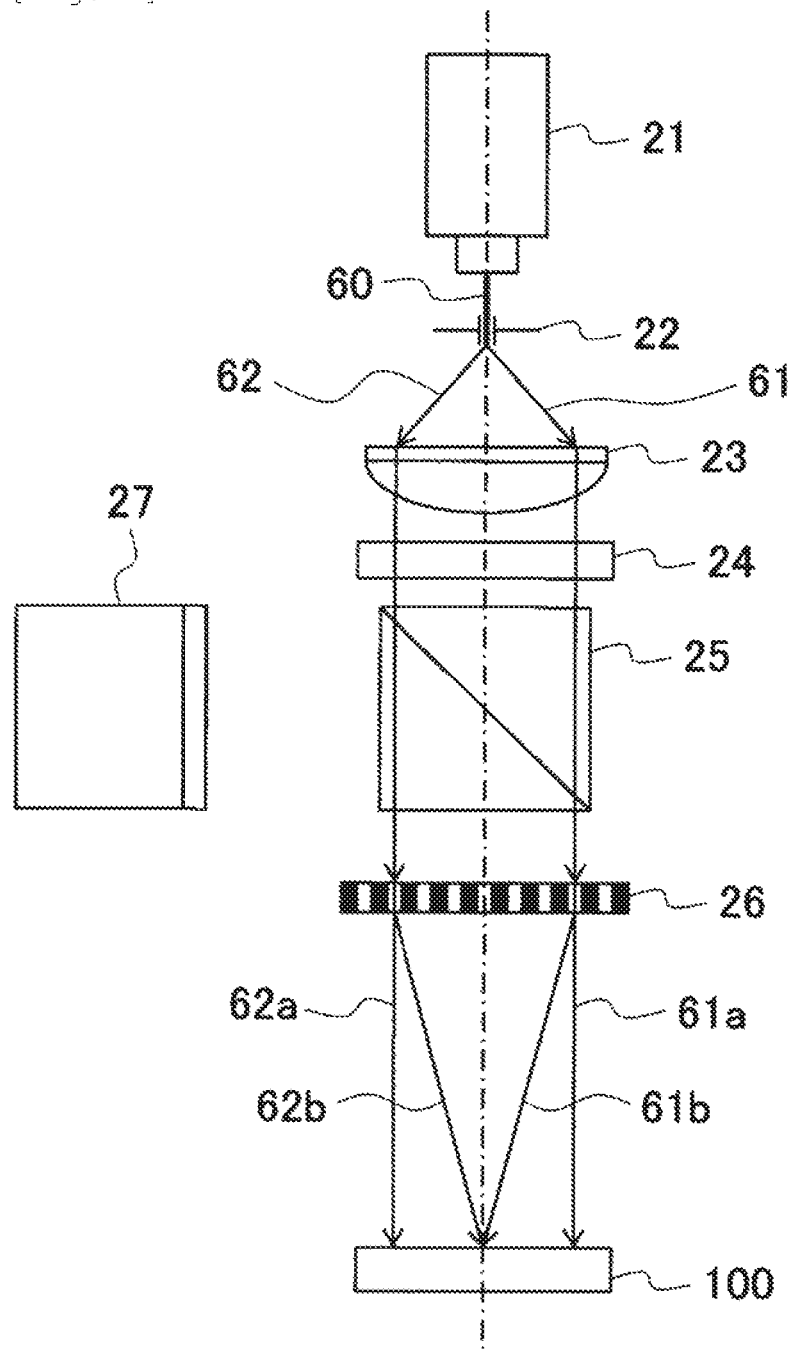

[Fig. 8]
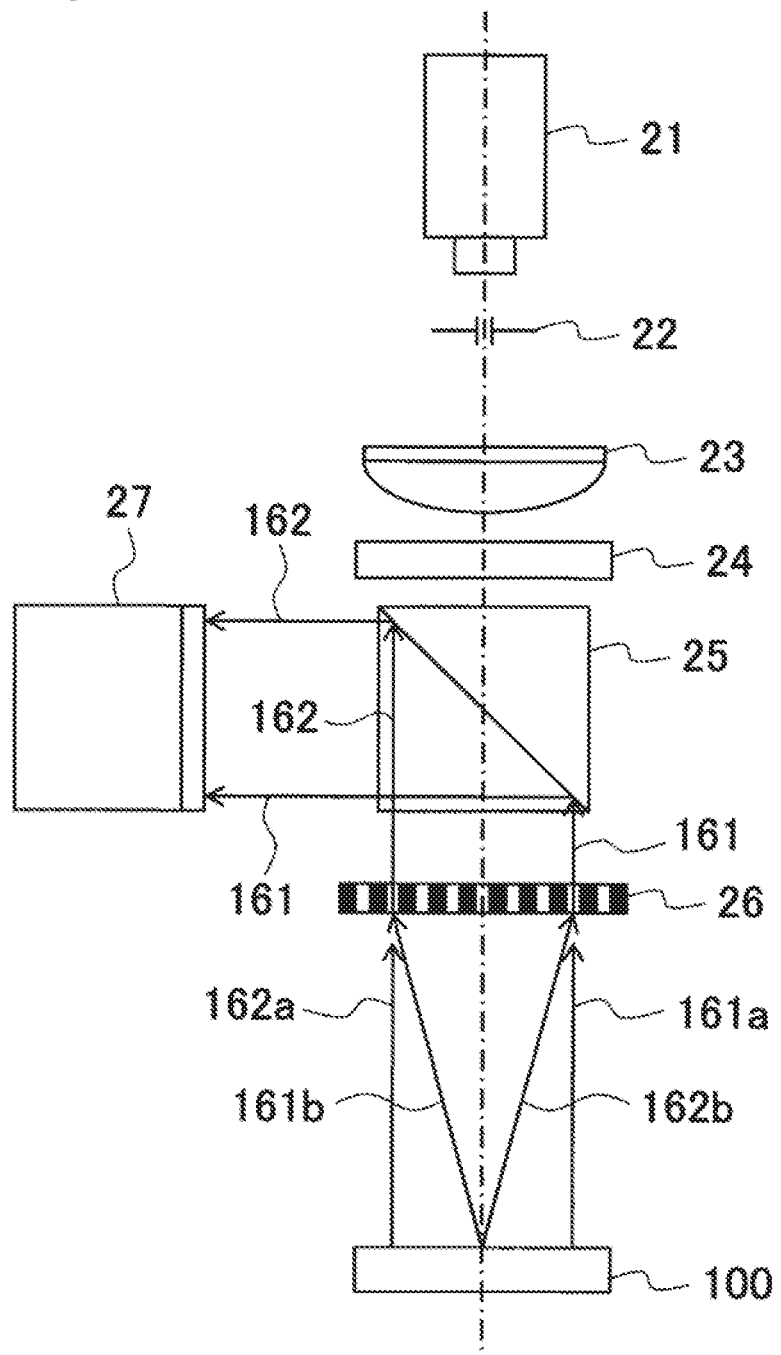

[Fig. 9]
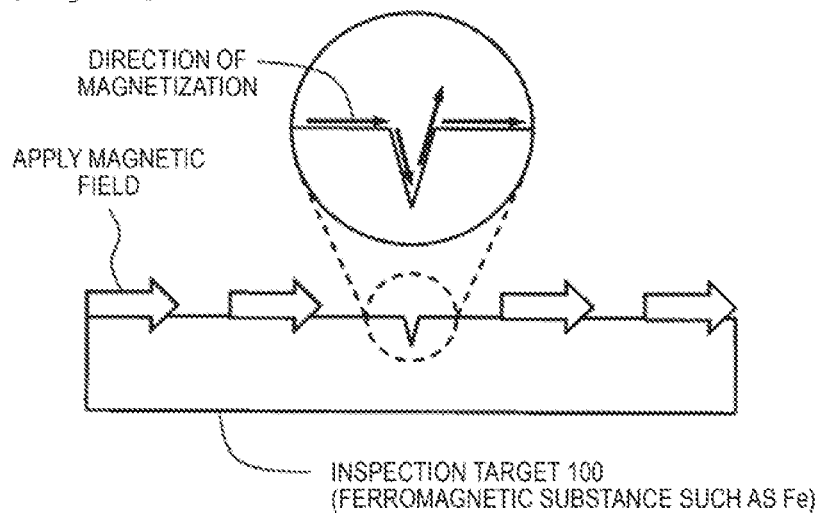
[Fig. 10]
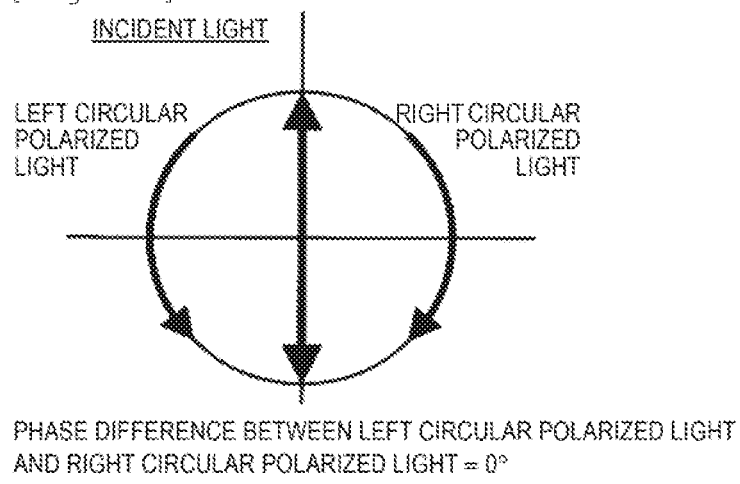
PHASE DIFFERENCE BETWEEN LEFT CIRCULAR POLARIZED LIGHT
AND RIGHT CIRCULAR POLARIZED LIGHT = 0°

[Fig. 11]
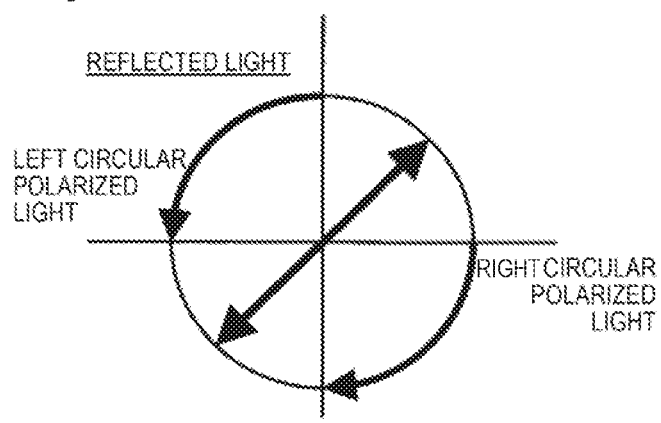
PHASE DIFFERENCE BETWEEN LEFT CIRCULAR POLARIZED LIGHT
AND RIGHT CIRCULAR POLARIZED LIGHT = 90°
ROTATION ANGLE OF PLANE OF POLARIZATION = 45°
[Fig. 12]
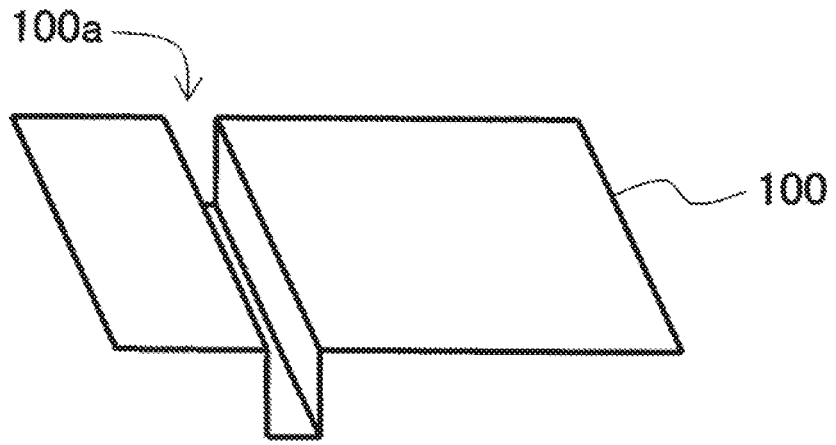

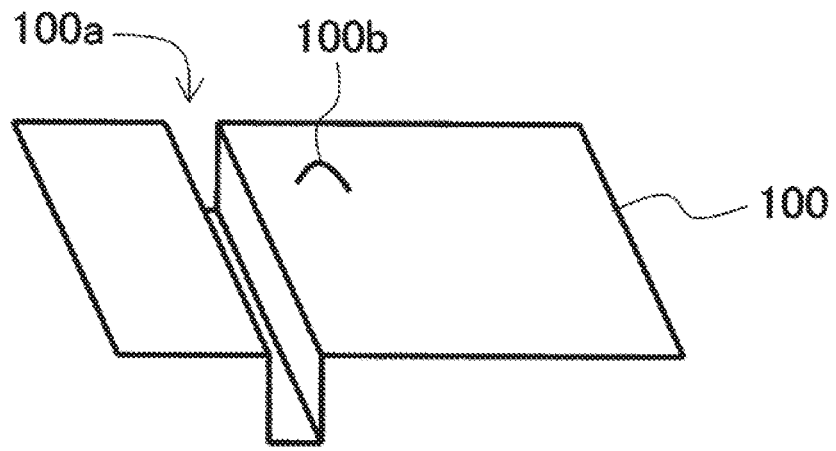
[Fig. 13]
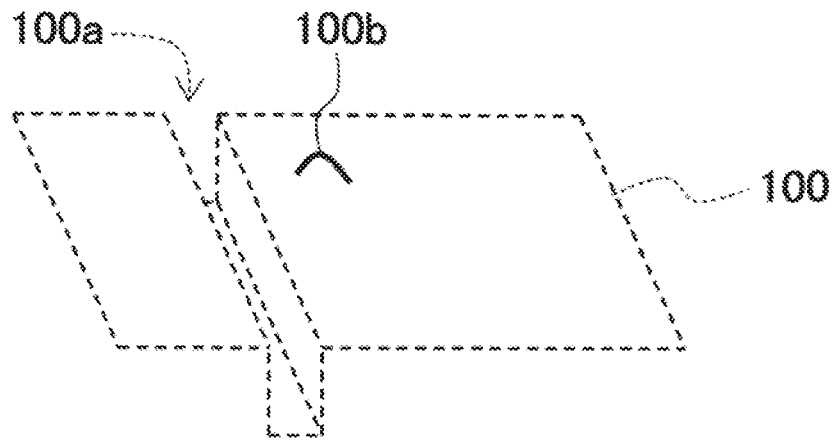
[Fig. 14]

DEFECT INSPECTION DEVICE AND DEFECT INSPECTION METHOD

TECHNICAL FIELD

The present invention relates to a defect inspection device and a defect inspection method for detecting a characteristic change (defect) such as a crack or a material change of a surface or an inside of an inspection target.

BACKGROUND ART

In a non-destructive inspection method using a magnetic field, a metal material, which is an inspection target object (inspection target), is irradiated with the magnetic field by energization to an excitation coil or a permanent magnet, a difference in magnetic field distribution caused by a characteristic change (hereinafter, referred to as a defect) such as a crack or a material change is detected by a magnetic sensor, and the defect is detected. For example, a leakage magnetic flux method, an eddy current flaw detection method, and the like are known. The leakage magnetic flux method is to infiltrate a magnetic flux into an inside of an inspection target using a direct current (DC) magnetic field or low frequency excitation in which magnetic field intensity does not generally change with time and to detect the magnetic flux leaking from a metal, which is the inspection target, in a vicinity of a crack by the magnetic sensor. The eddy current flaw detection method is to generate a magnetic flux of which a current value changes with time by supplying a current of which a current value changes with time to an excitation coil of an eddy current probe, to generate an eddy current by bringing the eddy current probe close to the metal, which is the inspection target, and to obtain a change of the eddy current as a detection signal by the magnetic sensor.

As a method of detecting a change of the magnetic field, in addition to a method of mechanically scanning a surface of the inspection target using a magnetic sensor such as a coil or a hall sensor, there is an inspection method which introduces a detection method for mapping spatial distribution of the magnetic field as a two-dimensional image using a magneto optical effect. For example, PTL 1 (JP-A-2014-153318) discloses a technique in which a magnetic thin film is disposed as a magnetic transfer film on an inspection surface of the inspection target, response light, which is reflected light obtained by irradiating the magnetic thin film with light, is imaged by a camera, and magnetic field distribution changed by the defect is acquired as an image and evaluated.

CITATION LIST

Patent Literature

PTL 1: JP-A-2014-153318

SUMMARY OF INVENTION

Technical Problem

The magneto optical effect used in the related art is a physical phenomenon in which a polarization angle of light emitted according to a magnetization state of a magnetic material in a case where light is applied to the target magnetic material is rotated. Faraday effect is related to transmitted light and Kerr effect is related to reflected light. In the magneto optical effect, since the amount of rotation of the polarization angle is sensitivity with respect to a magnetic field, it is possible to detect the magnetic field changed by the defect as the amount of rotation of a deflection angle and to use the magnetic field as information showing presence or absence of the defect.

However, the above described technique in the related art has the following problems.

That is, in a case where a surface shape of the inspection target is not a plane surface, since a gap is formed between the magnetic thin film used as the magnetic transfer film and the inspection target, magnetic field distribution on the surface of the inspection target cannot be accurately transferred onto the magnetic thin film and it is difficult to accurately detect the defect. In addition, since rotation of the polarization angle of light applied to the inspection target occurs not only by magnetic field distribution of the inspection target but also by an incidence angle of the light to the inspection target, it is further difficult to detect the defect because rotation of the polarization angle caused by the surface shape of the inspection target and rotation of a deflection angle caused by a change of magnetic field distribution by the defect are mixed in a case where the surface shape of the inspection target is not a plane surface.

The present invention is for view of the described above. An object of the present invention is to provide a defect inspection device and a defect inspection method capable of suppressing deterioration of measurement accuracy of magnetic field distribution caused by the surface shape of the inspection target and improving defect detection accuracy.

Solution to Problem

In order to achieve the above described object, according to the present invention, there is provided a defect inspection device which includes a shape measurement unit which measures a surface shape of an inspection target using light applied to the inspection target via a spatial light phase modulator based on an interference state of reflected light from the inspection target obtained via the spatial light phase modulator, a magnetic field distribution measurement unit which measures magnetization distribution of a surface of the inspection target magnetized by an excitation device for magnetizing the inspection target using light applied to the inspection target via the spatial light phase modulator based on an interference state of reflected light from the inspection target obtained via the spatial light phase modulator, and a data separation unit which separates data of a magnetic field specific portion which exists on the surface of the inspection target from magnetic field distribution data which is a measurement result of magnetic field distribution of the inspection target obtained by the magnetic field distribution measurement unit based on surface shape data which is a measurement result of the surface shape of the inspection target obtained by the shape measurement unit.

Advantageous Effects of Invention

According to the present invention, it is possible to suppress deterioration of measurement accuracy of magnetic field distribution generated by the surface shape of the inspection target and to improve defect detection accuracy.

BRIEF DESCRIPTION OF DRAWINGS

FIG. 1 is a diagram schematically showing an overall configuration of a defect inspection device according to an embodiment of the present invention.

FIG. 2 is a function block diagram schematically showing the overall configuration of the defect inspection device.

FIG. 3 is a diagram showing an optical path from a fresnel zone plate to a focus point.

FIG. 4 shows an example of the fresnel zone plate and is a diagram expressed by a graph showing a relationship between a distance from an optical axis and a refractive index.

FIG. 5 shows an example of the fresnel zone plate and is a diagram expressed by a two-dimensional display.

FIG. 6 is a diagram for explaining light propagation in the present embodiment and is a diagram showing irradiation light to an inspection target and reflected light from the inspection target.

FIG. 7 is a diagram for explaining light propagation in the present embodiment and is a diagram showing extracted irradiation light to the inspection target.

FIG. 8 is a diagram for explaining light propagation in the present embodiment and is a diagram showing extracted light reflected from the inspection target.

FIG. 9 is a diagram schematically showing a state in which a magnetic field is applied to an example of the inspection target of which a surface has a defect.

FIG. 10 is a diagram showing an example of phase modulation by a magneto optical effect.

FIG. 11 is a diagram showing an example of phase modulation by the magneto optical effect.

FIG. 12 is a diagram showing an example of a surface shape image obtained based on surface shape data.

FIG. 13 is a diagram showing an example of a magnetic field distribution image obtained based on magnetic field distribution data.

FIG. 14 is a diagram showing an example of a defect detection image obtained based on magnetic field specific portion data.

DESCRIPTION OF EMBODIMENTS

Hereinafter, embodiments of the present invention will be described with reference to drawings.

FIG. 1 is a diagram schematically showing an overall configuration of a defect inspection device according to an embodiment of the present invention. In addition, FIG. 2 is a function block diagram schematically showing the overall configuration of the defect inspection device.

In FIG. 1 and FIG. 2, the defect inspection device according to the present embodiment is schematically configured to include a control device 1, an inspection probe 2, an excitation device 3, a display device 4, and an input device 5.

The inspection probe 2 is for performing irradiation of inspection light to an inspection target 100, which is an inspection target object being configured to have ferromagnetic substance such as Fe, and detection of reflected light from the inspection target 100. The inspection probe 2 includes a laser light source 21 for emitting laser light, a spacial filter 22 for removing noise components from the laser light emitted from the laser light source 21 to shape the laser light, obtaining a Gaussian beam closer to an ideal, and expanding the beam at a predetermined angle, a collimator lens 23 for adjusting the light shaped by the spacial filter 22 to parallel light(light beam), a ¼ wavelength plate 24 for converting the parallel light from the collimator lens 23 to circular polarized light, a beam splitter 25 for splitting the incident light beam into transmitted light and reflected light, a spatial light phase modulator 26 for modulating spatial distribution of a phase of an incident circular polarized light beam transmitted through the beam splitter 25 from the ¼ wavelength plate 24, and a camera 27 for imaging light, which is reflected light from the inspection target 100 of light applied to the inspection target 100 via the spatial light phase modulator 26, reflected by the beam splitter 25 via the spatial light phase modulator 26.

The spatial light phase modulator 26 and a modulation signal generator 28 constitute a modulation switching unit 29. An operation of the spatial light phase modulator 26 is controlled by a modulation signal generated by the modulation signal generator 28 based on a control signal from an overall control unit 11 of the control device 1 described below. The spatial light phase modulator 26 has a function for performing modification of modulation contents or switching of presence or absence of modulation of transmitted light based on the modulation signal from the modulation signal generator 28. The spatial light phase modulator 26 is configured to include, for example, a liquid crystal layer. The spatial light phase modulator 26 implements a function such as diffraction grating in which desired phase modulation occurs and implements a function for switching presence or absence of phase modulation with respect to transmitted light by controlling the liquid crystal layer with a pixel as a unit by the modulation signal. The spatial light phase modulator 26 in the present embodiment is controlled so as to have a function such as phase modulation by a fresnel zone plate described below.

The excitation device 3 magnetizes the inspection target 100 into an alternating current (AC) by irradiating the inspection target 100 with a magnetic field of alternating current. The excitation device 3 includes an AC excitation power supply 32 for generating AC excitation current based on the control signal from the overall control unit 11 of the control device 1 described below and an excitation coil 31 for generating a magnetic field based on the excitation current from the AC excitation power supply 32 and applying the magnetic field to the generated inspection target 100. Information of excitation current generated by the AC excitation power supply 32, in other words, information of the magnetic field generated and applied to the inspection target 100 by the excitation coil 31 is sent to the overall control unit 11 with time information thereof. In a case where the control signal from the overall control unit 11 of the control device 1 is a control signal which does not generate excitation current, since excitation current is not also generated by the AC excitation power supply 32 and a magnetic field is not generated by the excitation coil 31, it is possible to make a state (magnetic field non-applied state) in which the magnetic field is not applied to the inspection target 100.

The control device 1 is for performing an operation control of the defect inspection device. The control device 1 includes the overall control unit 11 for controlling an overall operation of the defect inspection device having the control device 1, a magnetic field distribution data generating unit 12 for generating magnetic field distribution data as a measurement result of magnetic field distribution on a surface of the inspection target 100 based on an interference state of reflected light obtained as luminance data of an image captured by the camera 27 of the inspection probe 2, a surface shape data generating unit 14 for generating surface shape data as a measurement result of a surface shape on the surface of the inspection target 100 based on an interference state of reflected light obtained as luminance data of an image captured by the camera 27 of the inspection probe 2, and a data separation unit 17 for separating data (magnetic field specific portion data) of a magnetic field specific portion which exists on the surface of the inspection target 100 from magnetic field distribution data based on the surface shape data. Here, the magnetic field specific portion is a portion in which a change of magnetic field distribution which is not caused by the surface shape of the inspection target 100 occurs. The magnetic field specific portion is a portion which is predicted to have a characteristic change (hereinafter, referred to as a defect) such as a crack or a material change on the surface (or inside of a periphery of the surface) of the inspection target 100.

The data separation unit 17 includes a magnetic field distribution data storage unit 13 for storing magnetic field distribution data generated by the magnetic field distribution data generating unit 12, a surface shape data storage unit 15 for storing surface shape data generated by the surface shape data generating unit 14, and a difference calculation unit 16 for calculating difference between the magnetic field distribution data and the surface shape data.

The input device 5 is configured to include a mouse or a keyboard. The input device 5 is used, for example, for input of various setting values or operation instructions in the defect inspection device based on various setting screens or other information displayed on the display device 5.

In the display device 4, for example, a surface shape image based on the surface shape data of the inspection target 100, a magnetic field distribution image based on the magnetic field distribution data, or a defect detection image based on the magnetic field specific portion data is displayed in addition to various setting screens.

In the above, a surface shape measurement unit is configured to include the laser light source 21, the spacial filter 22, the collimator lens 23, the ¼ wavelength plate 24, the beam splitter 25, the spatial light phase modulator 26, the camera 27, and the surface shape data generating unit 14. The surface shape measurement unit measures the surface shape of the inspection target 100 using light applied to the inspection target 100 via the spatial light phase modulator 26 based on an interference state of reflected light from the inspection target 100 obtained via the spatial light phase modulator 26. A magnetic field distribution measurement unit is configured to include the laser light source 21, the spacial filter 22, the collimator lens 23, the ¼ wavelength plate 24, the beam splitter 25, the spatial light phase modulator 26, the excitation device 3, the camera 27, and the magnetic field distribution data generating unit 12. The magnetic field distribution measurement unit measures magnetization distribution of the inspection target 100 using light applied to the inspection target 100 via the spatial light phase modulator 26 based on an interference state of reflected light from the inspection target 100 obtained via the spatial light phase modulator 26.

Here, the fresnel zone plate in which a function is implemented by the spatial light phase modulator 26 in the present embodiment will be described with reference to FIGS. 3 to 5.

FIG. 3 is a diagram showing an optical path from the fresnel zone plate to a focus point. In addition, FIGS. 4 and 5 show an example of the fresnel zone plate. FIG. 4 is a diagram expressed by a graph showing a relationship between a distance from an optical axis and a refractive index. FIG. 5 is a diagram expressed by a two-dimensional display.

The fresnel zone plate can be expressed by distribution of interference fringes formed when light emitted from a certain point reaches a plane surface.

In FIG. 3, Φ is a diameter of the fresnel zone plate, f is a focal length, r is a distance from the fresnel zone plate to a focus point, θ is an angle between an optical axis and a line segment of r, n1 and n2 are refractive indexes of respective portions of the fresnel zone plate.

Here, if distribution of interference fringes is A and a wave number is k=(2π/λ), with an origin of the Fresnel zone plate as an origin (x, y)=(0, 0), respective coordinates (x, y) and the distance r to a focal point are calculated by the following (Expression 1). In addition, distribution of interference fringes is calculated by the following (Expression 2).

$$r = \sqrt{f^2 + \sqrt{x^2 + y^2}} \qquad \text{(Expression 1)}$$

$$A_{(x,y)} = \frac{\cos(kr)}{r} \qquad \text{(Expression 2)}$$

Based on (Expression 1) and (Expression 2) described above, a refractive index of each of the portions of the fresnel zone plate is calculated (see FIG. 4) and it is possible to define the fresnel zone plate (see FIG. 5) based on high and low of the refractive index by binarizing the refractive index with a threshold value=0.

FIGS. 6 to 8 are diagrams for explaining light propagation in the present embodiment and are diagrams schematically showing a configuration of an inspection probe 2 with the inspection target. FIG. 6 is a diagram showing irradiation light to the inspection target and reflected light from the inspection target. FIG. 7 is a diagram showing irradiation light to the inspection target extracted. FIG. 8 is a diagram showing reflected light from the inspection target extracted. In FIGS. 6 to 8, for a purpose of explaining a principle of the present invention, a case where the inspection target 100 is a plane surface perpendicular to an optical axis of the irradiation light is exemplified.

In FIGS. 6 to 8, laser light 60 emitted from the laser light source 21 is incident to the spacial filter 22, is shaped by removing noise components thereof, is expanded at a predetermined angle, and is adjusted to be parallel light (light beam) by the collimator lens 23. Here, if lights which are propagated to positions symmetrical with respect to an optical axis 21a are light beams 61 and 62, the light beams 61 and 62 adjusted to the parallel light by the collimator lens 23 are converted to circular polarized lights by the ¼ wavelength plate 24 and are incident to the beam splitter 25. The light beam incident from the ¼ wavelength plate 24 to the beam splitter 25 is split into the light beams 61 and 62 and reflected light (not shown) and the light beams 61 and 62 among the light beams 61 and 62 and the reflected light are incident to the spatial light phase modulator 26.

In a case where the spatial light phase modulator 26 is controlled by the overall control unit 11 so as to function as the fresnel zone plate, if the light beam 61 is transmitted through the spatial light phase modulator 26, transmitted light 61a (0 order light) propagated along the optical axis 21a and diffracted light 61b (1 order diffracted light) diffracted and propagated in a direction of an intersection with the optical axis 21a of the inspection target 100 is generated (see FIG. 7). In the same manner, if the light beam 62 is transmitted through the spatial light phase modulator 26, transmitted light 62a (0 order light) propagated along the optical axis 21a and diffracted light 62b (1 order diffracted light) diffracted and propagated in a direction of an intersection with the optical axis 21a of the inspection target 100 is generated (see FIG. 7).

On the surface of the inspection target 100, the transmitted light 61a is reflected in a direction along the optical axis 21a (reflected light 161a) and the diffracted light 61b is reflected in a direction of a position through which the light beam 62 of the spatial light phase modulator 26 is transmitted (reflected light 161b) (see FIG. 8). In the same manner, on the surface of the inspection target 100, the transmitted light 62a is reflected in a direction along the optical axis 21a (reflected light 162a) and the diffracted light 61b is reflected in a direction of a position through which the light beam 61 of the spatial light phase modulator 26 is transmitted (reflected light 162b) (see FIG. 8). At this time, phases of the reflected light 161a, 161b, 162a, and 162b are respectively changed by the surface shape and a magnetization state of the inspection target 100.

If the reflected light 161a and the reflected light 162b are transmitted through the spatial light phase modulator 26, diffracted light of the reflected light 162b propagated along the optical axis 21a and transmitted light of the reflected light 161a are reflected by the beam splitter 25 and are imaged by the camera 27 as a light beam 161. In the same manner, If the reflected light 162a and the reflected light 161b are transmitted through the spatial light phase modulator 26, diffracted light of the reflected light 161b propagated along the optical axis 21a and transmitted light of the reflected light 162a are reflected by the beam splitter 25 and are imaged by the camera 27 as a light beam 162.

Reflected light from the inspection target 100 of transmitted light (0 order light) in the spatial light phase modulator 26 in the present embodiment is object light and reflected light from the inspection target 100 of diffracted light (1 order diffracted light) is reference light. In the light beams 161 and 162 imaged by the camera 27, a phase difference between the reflected light 161a and the reflected light 162b and a phase difference between the reflected light 162a and the reflected light 161b (that is, phase difference between object light and reference light) respectively appear as a change of interference light intensity. That is, data of phase difference distribution is obtained based on distribution image data of interference light intensity obtained by the camera 27 and surface shape data or magnetic field distribution data is obtained based on the data of phase difference distribution.

The same manner applies to other light beams propagated in a direction along the optical axis 21a via the collimator lens 23.

FIG. 9 is a diagram schematically showing a state in which a magnetic field is applied to an example of the inspection target having the defect on a surface. FIGS. 10 and 11 are diagrams showing an example of phase modulation by a magneto optical effect.

In FIG. 9, in a case where a magnetic field is applied to the surface of the inspection target 100, it is understood that a direction of magnetization in a position of the defect or the like is different from directions of magnetization in the other portions. That is, as shown in FIGS. 10 and 11, phase modulation in Kerr effect of a phase (see FIG. 11) in reflected light with respect to a phase (see FIG. 10) in incident light differs between a defect position and the other positions, the defect is to be detected based on such knowledge in the present embodiment.

Here, a defect inspection process of the defect inspection device in the present embodiment will be described.

FIG. 12 is a diagram showing an example of a surface shape image obtained based on the surface shape data. FIG. 13 is a diagram showing an example of a magnetic field distribution image obtained based on the magnetic field distribution data. FIG. 14 is a diagram showing an example of a defect detection image obtained based on the magnetic field specific portion data.

The defect inspection process in the present embodiment is configured to include a surface shape measurement step, a magnetic field distribution measurement step, and a data separation step. The surface shape measurement step is a step in which the surface shape of the inspection target 100 is measured using light applied to the inspection target via the spatial light phase modulator 26 based on an interference state of reflected light from the inspection target 100 obtained via the spatial light phase modulator 26. The magnetic field distribution measurement step is a step in which magnetic field distribution of the surface of the inspection target 100 magnetized by the excitation device 3 for magnetizing the inspection target 100 is measured using light applied to the inspection target 100 through the spatial light phase modulator 26 based on an interference state of reflected light from the inspection target 100 obtained via the spatial light phase modulator 26. The data separation step is a step in which data of a magnetic field specific portion 100b which exists on the surface of the inspection target 100 is separated from magnetic field distribution data which is a measurement result of magnetic field distribution of the inspection target 100 based on surface shape data which is a measurement result of the surface shape of the inspection target 100.

In the surface shape measurement step, irradiation of light to the inspection target 100 is performed and reflected light is imaged by the camera 27 via the spatial light phase modulator 26 which functions as the fresnel plate in a state in which magnetization of the inspection target 100 is not performed by the excitation device 3 and surface shape data is obtained from an obtained image by the surface shape data generating unit 14. In the surface shape data generating unit 14, the surface shape (a position of each of portions in an optical axis direction, an angle formed with the optical axis of the surface, or the like) of the inspection target 100 is calculated based on an interference state of reflected light obtained as luminance data of an image obtained by the camera 27 and is stored in the surface shape data storage unit 15 as the surface shape data. The surface shape data obtained in this way shows information on the surface shape of the inspection target 100 and can be expressed as the surface shape image by predetermined processes (see FIG. 12).

In the magnetic field distribution measurement step, irradiation of light is performed to the inspection target 100 and reflected light via the spatial light phase modulator 26 which functions as the fresnel plate is imaged by the camera 27 in a state in which magnetization of the inspection target 100 is performed by the excitation device 3 and magnetic field distribution data is obtained from an obtained image by the magnetic field distribution data generating unit 12. In the magnetic field distribution data generating unit 12, magnetic field distribution (a direction of magnetization of each of the portions at application time of a magnetic field or the like) of the inspection target 100 is calculated based on an interference state of reflected light obtained as luminance data of an image obtained by the camera 27 and is stored in the magnetic field distribution data storage unit 13 as the magnetic field distribution data. The magnetic field distribution data obtained in this way can include information on both sides of the magnetic field specific portion 100b considered to be caused by the surface shape, the defect, and the like of the inspection target 100 and can be expressed as the magnetic field distribution image by predetermined processes (see FIG. 13).

In the data separation step, in the data separation unit 17, the magnetic field specific portion data including only the magnetic field specific portion 100b considered to be caused by the defect and the like is obtained by performing difference calculation between the magnetic field distribution data stored in the magnetic field distribution data storage unit 13 and the surface shape data stored in the surface shape data storage unit 15. The magnetic field specific portion data obtained in this way can be expressed as the defect detection image by predetermined processes (see FIG. 14).

The defect detection image obtained in the defect inspection process is stored in a storage unit included in the overall control unit 11 of the control device 1 and is displayed on the display device 4 or the like with the surface shape image or the magnetic field distribution image.

In the surface shape measurement step, it is possible to perform laser measurement for accurately measuring a position of the inspection target 100 with respect to the defect inspection device, error detection of the position of the inspection target 100 with respect to the defect inspection device, and the like by appropriately controlling phase modification of the spatial light phase modulator 26.

Operational effects of the present embodiment configured as described above will be described.

The magneto optical effect used in the related art is a physical phenomenon in which a polarization angle of light emitted according to a magnetization state of a magnetic material in a case where light is applied to the target magnetic material is rotated. Faraday effect is related to transmitted light and Kerr effect is related to reflected light. In the magneto optical effect, since the amount of rotation of the polarization angle is sensitivity with respect to a magnetic field, it is possible to detect the magnetic field changed by the defect as the amount of rotation of a deflection angle and to use the magnetic field as information showing presence or absence of the defect. However, in a case where a surface shape of the inspection target is not a plane surface, since a gap is formed between a magnetic thin film used as a magnetic transfer film and the inspection target, magnetic field distribution on the surface of the inspection target cannot be accurately transferred to the magnetic thin film and it is difficult to accurately detect the defect. In addition, since rotation of the polarization angle of light applied to the inspection target occurs not only by magnetic field distribution of the inspection target but also by an incidence angle of the light to the inspection target, it is further difficult to detect the defect because rotation of the polarization angle caused by the surface shape of the inspection target and rotation of a deflection angle caused by a change of magnetic field distribution by the defect are mixed in a case where the surface shape of the inspection target is not a plane surface.

The present embodiment is configured to measure the surface shape of the inspection target 100 using light applied to the inspection target via the spatial light phase modulator 26 based on an interference state of reflected light from the inspection target 100 obtained via the spatial light phase modulator 26, to measure magnetic field distribution of the surface of the inspection target 100 magnetized by the excitation device 3 for magnetizing the inspection target 100 using light applied to the inspection target 100 via the spatial light phase modulator 26 based on an interference state of reflected light from the inspection target 100 obtained via the spatial light phase modulator 26, and to separate data of the magnetic field specific portion 100b which exists on the surface of the inspection target 100 from magnetic field distribution data which is a measurement result of magnetic field distribution of the inspection target 100 based on surface shape data which is a measurement result of the surface shape of the inspection target 100. Thereby, it is possible to suppress deterioration of measurement accuracy of magnetic field distribution generated by the surface shape of the inspection target and to improve defect detection accuracy.

In addition, in the related art in which object light and reference light are generated through different paths, there is a problem that phase noise caused by a difference in an environment (humidity, fluctuation of air, or the like) between the paths of the object light and the reference light is superimposed. In the present embodiment, since the beam splitter 25 and the spatial light phase modulator 26 are disposed on the paths of irradiation light and reflected light to the surface of the inspection target 100, object light (0 order light) and reference light (1 order diffracted light) are transmitted through a path of the same environment, and phase noise is cancelled out, it is possible to perform defect detection with higher accuracy.

In addition, the surface shape measurement unit is configured to include the laser light source 21, the spacial filter 22 for shaping light emitted from the laser light source 21, the collimator lens 23 for adjusting the light from the spacial filter 22 to parallel light, the ¼ wavelength plate 24 for converting the parallel light from the collimator lens 23 to a circular polarized light beam, the beam splitter 25 for splitting the incident light into transmitted light and reflected light, the spatial light phase modulator 26 for modulating spatial distribution of a phase of the incident circular polarized light beam transmitted through the beam splitter 25 from the ¼ wavelength plate 24, the camera 27 for imaging light, which is reflected light from the inspection target 100 of light applied to the inspection target 100 via the spatial light phase modulator 26, reflected by the beam splitter 25 via the spatial light phase modulator 26, and the surface shape data generating unit 14 for generating the surface shape data of the surface of the inspection target 100 based on an interference state of reflected light obtained as luminance data of an image captured by the camera 27. Thereby, it is possible to accurately measure the surface shape of the inspection target 100.

REFERENCE SIGNS LIST 1 control device
2 inspection probe
3 excitation device
4 display device
5 input device
11 overall control unit
12 magnetic field distribution data generating unit
13 magnetic field distribution data storage unit
14 surface shape data generating unit
15 surface shape data storage unit
16 difference calculation unit
17 data separation unit
21 laser light source
22 spacial filter
23 collimator lens
24 ¼ wavelength plate
25 beam splitter
26 spatial light phase modulator
27 camera
28 modulation signal generator
29 modulation switching unit
31 excitation coil
32 AC excitation power supply
100 inspection target (inspection target object)

The invention claimed is:

1. A defect inspection device comprising:
a surface shape measurement unit which measures a surface shape of an inspection target using light applied to the inspection target via a spatial light phase modulator based on an interference state of reflected light from the inspection target obtained via the spatial light phase modulator;
a magnetic field distribution measurement unit which measures magnetic field distribution of a surface of the inspection target magnetized by an excitation device for magnetizing the inspection target using light applied to the inspection target via the spatial light phase modulator based on an interference state of reflected light from the inspection target obtained via the spatial light phase modulator; and
a data separation unit which separates data of a magnetic field specific portion which exists on the surface of the inspection target from magnetic field distribution data which is a measurement result of magnetic field distribution of the inspection target obtained by the magnetic field distribution measurement unit based on surface shape data which is a measurement result of the surface shape of the inspection target obtained by the surface shape measurement unit,
wherein the surface shape measurement unit includes
a laser light source;
a spatial filter for shaping light emitted from the laser light source;
a collimator lens for adjusting light from the spatial filter to parallel light;
a ¼ wavelength plate for converting the parallel light from the collimator lens to a circular polarized light beam;
a beam splitter for splitting incident light into transmitted light and reflected light;
a spatial light phase modulator for modulating spatial distribution of a phase of the incident circular polarized light beam transmitted through the beam splitter from the ¼ wavelength plate;
a camera for imaging light, which is reflected light from the inspection target of light applied to the inspection target via the spatial light phase modulator, reflected by the beam splitter via the spatial light phase modulator; and
a surface shape data generating unit for generating surface shape data of the surface of the inspection target based on an interference state of reflected light obtained as luminance data of an image captured by the camera.

2. The defect inspection device according to claim 1, wherein the data separation unit includes
a surface shape data storage unit for storing the surface shape data of the inspection target obtained by the surface shape measurement unit,
a magnetic field distribution data storage unit for storing the magnetic field distribution data of the inspection target obtained by the magnetic field distribution measurement unit, and
a difference calculation unit for performing difference calculation between the magnetic field distribution data and the surface shape data.

3. The defect inspection device according to claim 1, wherein the magnetic field distribution measurement unit and the surface shape measurement unit include
the beam splitter for splitting light, which is incident via the collimator lens for adjusting light from the light source to parallel light and the ¼ wavelength plate for converting the parallel light to the circular polarized light beam, into transmitted light and reflected light,
the spatial light phase modulator for modulating spatial distribution of the phase of the incident circular polarized light beam transmitted through the beam splitter from the ¼ wavelength plate, and
the camera for imaging light, which is reflected light as object light and reference light from the inspection target of light applied to the inspection target via the spatial light phase modulator, reflected by the beam splitter via the spatial light phase modulator,
wherein the surface shape measurement unit and the magnetic field distribution measurement unit measure the surface shape and the magnetic field distribution of the inspection target based on an interference state of the object light and the reference light from the inspection target.

4. The defect inspection device according to claim 1, further comprising:
a modulation switching control unit which controls the spatial light phase modulator and switches presence or absence of modulation of light applied to the inspection target; and
a distance measurement function which obtains a position of an optical axis direction of the inspection target by irradiation of light to the inspection target in a state in which modulation of light is not performed by the spatial light phase modulator.

5. A defect inspection device comprising:
a surface shape measurement unit which measures a surface shape of an inspection target using light applied to the inspection target via a spatial light phase modulator based on an interference state of reflected light from the inspection target obtained via the spatial light phase modulator;
a magnetic field distribution measurement unit which measures magnetic field distribution of a surface of the inspection target magnetized by an excitation device for magnetizing the inspection target using light applied to the inspection target via the spatial light phase modulator based on an interference state of reflected light from the inspection target obtained via the spatial light phase modulator; and
a data separation unit which separates data of a magnetic field specific portion which exists on the surface of the inspection target from magnetic field distribution data which is a measurement result of magnetic field distribution of the inspection target obtained by the magnetic field distribution measurement unit based on surface shape data which is a measurement result of the surface shape of the inspection target obtained by the surface shape measurement unit,
wherein the surface shape measurement unit includes
a laser light source;
a spatial filter for shaping light emitted from the laser light source;
a collimator lens for adjusting light from the spatial filter to parallel light;
a ¼ wavelength plate for converting the parallel light from the collimator lens to a circular polarized light beam;
a beam splitter for splitting incident light into transmitted light and reflected light;
a spatial light phase modulator for modulating spatial distribution of a phase of the incident circular polarized light beam transmitted through the beam splitter from the ¼ wavelength plate;

a camera for imaging light, which is reflected light from the inspection target of light applied to the inspection target via the spatial light phase modulator, reflected by the beam splitter via the spatial light phase modulator; and a surface shape data generating unit for generating surface shape data of the surface of the inspection target based on an interference state of reflected light obtained as luminance data of an image captured by the camera, and wherein the magnetic field distribution measurement unit includes the laser light source;

the spatial filter for shaping light emitted from the laser light source;

the collimator lens for adjusting light from the spatial filter to parallel light;

the ¼ wavelength plate for converting the parallel light from the collimator lens to the circular polarized light beam;

the beam splitter for splitting incident light into transmitted light and reflected light;

the spatial light phase modulator for modulating spatial distribution of the phase of the incident circular polarized light beam transmitted through the beam splitter from the ¼ wavelength plate;

the camera for imaging light, which is reflected light from the inspection target of light applied to the inspection target via the spatial light phase modulator, reflected by the beam splitter via the spatial light phase modulator;

an excitation device having an excitation coil for magnetizing the inspection target and an AC excitation power supply for applying excitation current to the excitation coil; and a magnetic field distribution data generating unit for generating magnetic field distribution data of the surface of the inspection target based on an interference state of reflected light obtained as luminance data of an image captured by the camera.

6. A defect inspection device comprising:

a laser light source;

a spatial filter for shaping light emitted from the laser light source;

a collimator lens for adjusting light from the spatial filter to parallel light;

a ¼ wavelength plate for converting the parallel light from the collimator lens to a circular polarized light beam;

a beam splitter for splitting incident light into transmitted light and reflected light;

a spatial light phase modulator for modulating spatial distribution of a phase of the incident circular polarized light beam transmitted through the beam splitter from the ¼ wavelength plate;

a camera for imaging light, which is reflected light from an inspection target of light applied to the inspection target via the spatial light phase modulator, reflected by the beam splitter via the spatial light phase modulator;

an excitation device for magnetizing the inspection target;

a magnetization switching control unit which controls the excitation device and switches presence or absence of magnetization of the inspection target; and a data separation unit which separates data of a magnetic field specific portion which exists on a surface of the inspection target from magnetic field distribution data which is a measurement result of magnetic field distribution of the inspection target obtained by a magnetic field distribution measurement unit for measuring magnetic field distribution of the surface of the inspection target based on an interference state of reflected light from the inspection target, based on surface shape data which is a measurement result of a surface shape of the inspection target obtained by a surface shape measurement unit for measuring the surface shape of the inspection target based on an interference state of reflected light from the inspection target, wherein the surface shape measurement unit includes the laser light source;

the spatial filter for shaping light emitted from the laser light source;

the collimator lens for adjusting light from the spatial filter to parallel light;

the ¼ wavelength plate for converting the parallel light from the collimator lens to the circular polarized light beam;

the beam splitter for splitting incident light into transmitted light and reflected light;

the spatial light phase modulator for modulating spatial distribution of the phase of the incident circular polarized light beam transmitted through the beam splitter from the ¼ wavelength plate;

the camera for imaging light, which is reflected light from the inspection target of light applied to the inspection target via the spatial light phase modulator, reflected by the beam splitter via the spatial light phase modulator; and a surface shape data generating unit for generating surface shape data of the surface of the inspection target based on an interference state of reflected light obtained as luminance data of an image captured by the camera.

7. A defect inspection method comprising:

a surface shape measurement step in which a surface shape of an inspection target is measured using a surface shape measurement unit using light applied to the inspection target via a spatial light phase modulator based on an interference state of reflected light from the inspection target obtained via the spatial light phase modulator;

a magnetic field distribution measurement step in which magnetic field distribution of a surface of the inspection target magnetized by an excitation device for magnetizing the inspection target is measured using light applied to the inspection target via the spatial light phase modulator based on an interference state of reflected light from the inspection target obtained via the spatial light phase modulator; and a data separation step in which data of a magnetic field specific portion which exists on the surface of the inspection target is separated from magnetic field distribution data which is a measurement result of magnetic field distribution of the inspection target based on surface shape data which is a measurement result of the surface shape of the inspection target, wherein the surface shape measurement unit includes a laser light source;

a spatial filter for shaping light emitted from the laser light source;

a collimator lens for adjusting light from the spatial filter to parallel light;

a ¼ wavelength plate for converting the parallel light from the collimator lens to a circular polarized light beam;
a beam splitter for splitting incident light into transmitted light and reflected light;
a spatial light phase modulator for modulating spatial distribution of a phase of the incident circular polarized light beam transmitted through the beam splitter from the ¼ wavelength plate;
a camera for imaging light, which is reflected light from the inspection target of light applied to the inspection target via the spatial light phase modulator, reflected by the beam splitter via the spatial light phase modulator; and
a surface shape data generating unit for generating surface shape data of the surface of the inspection target based on an interference state of reflected light obtained as luminance data of an image captured by the camera.

* * * * *